(12) United States Patent
Xia

(10) Patent No.: US 11,879,154 B2
(45) Date of Patent: Jan. 23, 2024

(54) PREPARATION METHOD OF HIGH-STABILITY SUPEROXIDE DISMUTASE WITH TRANSMEMBRANE CAPABILITY

(71) Applicant: Yong Xia, Jining (CN)

(72) Inventor: Yong Xia, Jining (CN)

( * ) Notice: Subject to any disclaimer, the term of this patent is extended or adjusted under 35 U.S.C. 154(b) by 20 days.

(21) Appl. No.: 17/563,794

(22) Filed: Dec. 28, 2021

(65) Prior Publication Data

US 2023/0002818 A1    Jan. 5, 2023

(30) Foreign Application Priority Data

Jun. 28, 2021   (CN) .......................... 202110719256.8

(51) Int. Cl.
*C12Q 1/6865*   (2018.01)
*C12N 9/02*    (2006.01)

(52) U.S. Cl.
CPC ......... *C12Q 1/6865* (2013.01); *C12N 9/0089* (2013.01); *C12Y 115/01001* (2013.01)

(58) Field of Classification Search
None
See application file for complete search history.

(56) References Cited

U.S. PATENT DOCUMENTS

| | | | | |
|---|---|---|---|---|
| 7,470,661 | B2 * | 12/2008 | Shone | C07K 14/33 424/94.1 |
| 2008/0267944 | A1 * | 10/2008 | Chudzinski-Tavassi | A61P 7/04 435/219 |

* cited by examiner

*Primary Examiner* — Richard G Hutson

(57) ABSTRACT

The present disclosure belongs to the technical field of genetic modification of an enzyme preparation and particularly relates to a preparation method of a high-stability superoxide dismutase with a transmembrane capability. The method includes the following steps: extracting mRNA from *Geobacillus stearothermophilus*, synthesizing cDNA by a reverse transcription method, amplifying a large number of coding regions of the cDNA by designing a specific primer, ligating the coding regions to an *E. coli* expression vector, and transforming the coding regions into engineering bacteria BL21 (DE3). A point mutation technology is used to enhance stability of the superoxide dismutase and a flexible polypeptide linker GGGSGGGS (SEQ ID NO: 11) is designed, such that a soluble fusion expression of a transmembrane peptide YGRKKRRQRRR (SEQ ID NO: 10) and the superoxide dismutase is successfully realized.

1 Claim, 14 Drawing Sheets

Specification includes a Sequence Listing.

Lane M1: DNA Marker
Lane 1-10: Monoclonal PCR identification

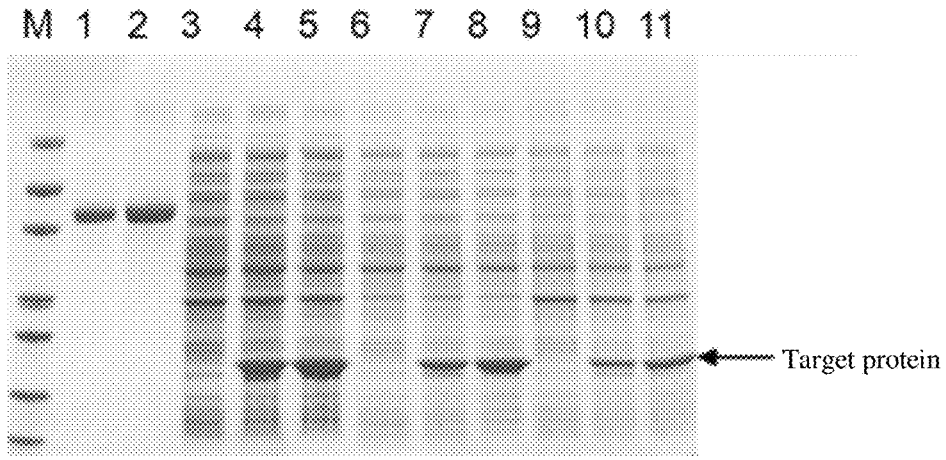

Lane Ml: protein Marker
Lane 1: BSA (1 μg)
Lane 2: BSA (2 μg)
Lane 3: before induction
Lane 4: induction at 16°C for 14 hours
Lane 5: induction at 37°C for 4 hours
Lane 6: supernatant after cell lysis before induction
Lane 7: supernatant after induction at 16°C for 14 hours and lysis
Lane 8: supernatant after induction at 37°C for 4 hours and lysis
Lane 9: precipitate after cell lysis before induction
Lane 10: precipitate after induction at 16°C for 14 hours and lysis
Lane 11: precipitate after induction at 37°C for 4 hours and lysis

FIG. 3

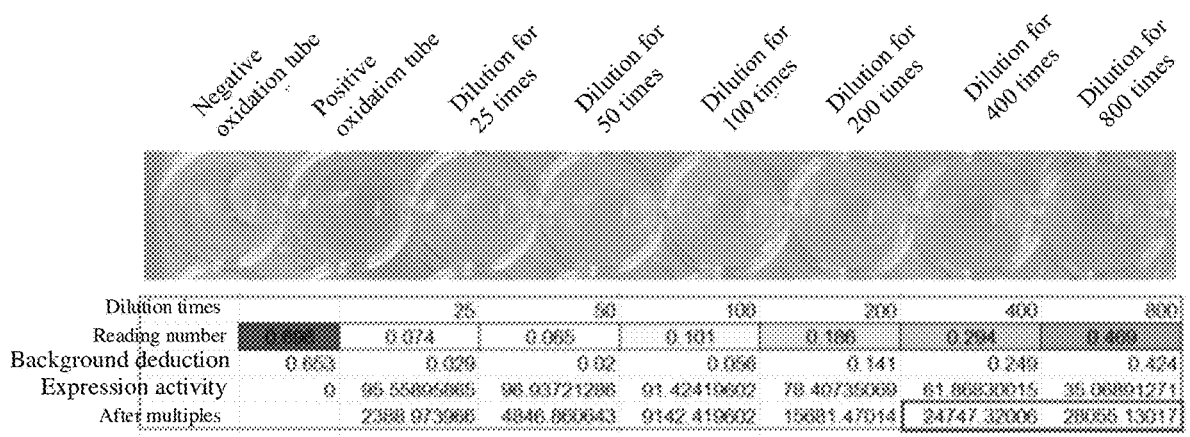

FIG. 4

SEQUENCE LISTING

```
<160> NUMBER OF SEQ ID NOS: 15

<210> SEQ ID NO 1
<211> LENGTH: 204
<212> TYPE: PRT
<213> ORGANISM: Artificial Sequence
<220> FEATURE:
<223> OTHER INFORMATION: Amino acid sequence of the SOD from the
      geobacillus stearothermophilus

<400> SEQUENCE: 1

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
            20                  25                  30

Asn Thr Tyr Val Thr Asn Leu Asn Ala Ala Leu Glu Gly His Pro Asp
        35                  40                  45

Leu Gln Asn Lys Ser Leu Glu Glu Leu Leu Ser Asn Leu Glu Ala Leu
    50                  55                  60

Pro Glu Ser Ile Arg Thr Ala Val Arg Asn Asn Gly Gly Gly His Ala
65                  70                  75                  80

Asn His Ser Leu Phe Trp Thr Ile Leu Ser Pro Asn Gly Gly Gly Glu
                85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Ala Gly Arg Phe Gly
        115                 120                 125

Ser Gly Trp Ala Trp Leu Val Val Asn Asn Gly Glu Leu Glu Ile Thr
    130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190
```

```
Glu Val Ala Lys Arg Tyr Ser Glu Ala Lys Ala Lys
        195                 200
```

<210> SEQ ID NO 2
<211> LENGTH: 25
<212> TYPE: DNA
<213> ORGANISM: Artificial Sequence
<220> FEATURE:
<223> OTHER INFORMATION: Captured upstream primer sequence for the SOD

<400> SEQUENCE: 2
catatgccct ttgaactacc agcat                                          25

<210> SEQ ID NO 3
<211> LENGTH: 25
<212> TYPE: DNA
<213> ORGANISM: Artificial Sequence
<220> FEATURE:
<223> OTHER INFORMATION: Captured downstream primer sequence for the SOD

<400> SEQUENCE: 3
aagcttcttc gctttcgcct cgctg                                          25

<210> SEQ ID NO 4
<211> LENGTH: 621
<212> TYPE: DNA
<213> ORGANISM: Artificial Sequence
<220> FEATURE:
<223> OTHER INFORMATION: DNA sequence coding the SOD

<400> SEQUENCE: 4
atgccctttg aactaccagc attaccctat ccctatgatg ctctagaacc gcacattgac     60
aaggagacca tgaacatcca ccacaccaag caccacaaca cctacgtgac caacctgaac    120
gcggcgctgg agggtcaccc ggacctgcag aacaaaagcc tggaggaact gctgagcaac    180
ctggaggcgt gccggaaaag catccgtacc gcggttcgta acaacggtgg cggtcacgcg    240
aaccacagcc tgttttggac catcctgagc ccgaacggcg gtggcgagcc gaccggtgaa    300
ctggcggacg cgattaacaa gaaattcggc agctttaccg cgttcaagga tgagtttagc    360
aaagcggcgg cgggtcgttt cggtagcggt tgggcgtggc tggttgtgaa caacggcgag    420
ctggaaatca ccagcacccc gaaccaggac agcccgatca tggagggcaa gaccccgatt    480
ctgggcctgg atgtgtggga acacgcgtac tatctgaaat accaaaaccg tcgtccggaa    540
tatattgcgg cgttctggaa tgtggtgaac tgggacgagg tggcgaagcg ttacagcgag    600
gcgaaagcga agtgaaagct t                                             621

<210> SEQ ID NO 5
<211> LENGTH: 22
<212> TYPE: DNA
<213> ORGANISM: Artificial Sequence
<220> FEATURE:
<223> OTHER INFORMATION: Upstream primer sequence for colony PCR

<400> SEQUENCE: 5
ttaccctatc cctatgatgc tc                                             22

<210> SEQ ID NO 6
<211> LENGTH: 18
<212> TYPE: DNA
<213> ORGANISM: Artificial Sequence
<220> FEATURE:
<223> OTHER INFORMATION: Downstream primer sequence for colony PCR

<400> SEQUENCE: 6
cccaaccgct accgaaac                                                       18

<210> SEQ ID NO 7
<211> LENGTH: 223
<212> TYPE: PRT
<213> ORGANISM: Artificial Sequence
<220> FEATURE:
<223> OTHER INFORMATION: Amino acid sequence of the SOD with a
      transmembrane capability

<400> SEQUENCE: 7

```
Met Pro Phe Glu Leu Pro Ala Leu Pro Tyr Pro Tyr Asp Ala Leu Glu
 1               5                  10                  15

Pro His Ile Gly Lys Glu Thr Met Asn Ile His His Thr Lys His His
             20                  25                  30

Asn Thr Tyr Val Thr Asn Leu Asn Ala Ala Leu Glu Gly His Pro Asp
         35                  40                  45

Leu Gln Asn Lys Ser Leu Glu Glu Leu Leu Ser Asn Leu Glu Ala Leu
     50                  55                  60

Pro Glu Ser Ile Arg Thr Ala Val Arg Asn Asn Gly Gly Gly His Ala
 65                  70                  75                  80

Asn His Ser Leu Phe Trp Thr Ile Leu Ser Pro Asn Gly Gly Gly Glu
                 85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Ala Gly Arg Phe Gly
        115                 120                 125

Ser Gly Trp Ala Trp Leu Val Val Asn Asn Gly Glu Asn Glu Ile Thr
    130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190

Glu Val Ala Lys Arg Tyr Ser Glu Ala Lys Ala Lys Gly Gly Gly Ser
        195                 200                 205

Gly Gly Gly Ser Tyr Gly Arg Lys Lys Arg Gln Arg Arg
    210                 215                 220
```

<210> SEQ ID NO 8
<211> LENGTH: 49
<212> TYPE: DNA
<213> ORGANISM: Artificial Sequence
<220> FEATURE:
<223> OTHER INFORMATION: Primer 1

<400> SEQUENCE: 8
ccataacttc ctcctccact tcctcctcca agctttcact tcgctttcg                     49

<210> SEQ ID NO 9
<211> LENGTH: 46
<212> TYPE: DNA
<213> ORGANISM: Artificial Sequence
<220> FEATURE:
<223> OTHER INFORMATION: Primer 2

<400> SEQUENCE: 9
tcgtaagaag cgccgtcaac gtcgccgtat tcgccggcct gagctc           46

<210> SEQ ID NO 10
<211> LENGTH: 11
<212> TYPE: PRT
<213> ORGANISM: Artificial Sequence
<220> FEATURE:
<223> OTHER INFORMATION: Amino acid sequence of the CPP

<400> SEQUENCE: 10

Tyr Gly Arg Lys Lys Arg Arg Gln Arg Arg Arg
1               5                   10

<210> SEQ ID NO 11
<211> LENGTH: 8
<212> TYPE: PRT
<213> ORGANISM: Artificial Sequence
<220> FEATURE:
<223> OTHER INFORMATION: Amino acid sequence of a flexible polypeptide
      linker

<400> SEQUENCE: 11

Gly Gly Gly Ser Gly Gly Gly Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Amino acid sequence of an optional flexible
      polypeptide linker

<400> SEQUENCE: 12

Gly Gly Gly Gly Ser
1               5

<210> SEQ ID NO 13
<211> LENGTH: 6
<212> TYPE: PRT
<213> ORGANISM: Artificial Sequence
<220> FEATURE:
<223> OTHER INFORMATION: Amino acid sequence of an optional flexible
      polypeptide linker

<400> SEQUENCE: 13

Gly Gly Ser Gly Gly Ser
1               5

<210> SEQ ID NO 14
<211> LENGTH: 5
<212> TYPE: PRT
<213> ORGANISM: Artificial Sequence
<220> FEATURE:
<223> OTHER INFORMATION: Amino acid sequence of an optional flexible
      polypeptide linker

<400> SEQUENCE: 14

Gly Gly Gly Gly Gly
1               5

<210> SEQ ID NO 15
<211> LENGTH: 8
<212> TYPE: PRT
<213> ORGANISM: Artificial Sequence
<220> FEATURE:
<223> OTHER INFORMATION: Amino acid sequence of a flexible polypeptide

```
    linker as a control

<400> SEQUENCE: 15

Ala Ala Ala Ser Ala Ala Ala Ser
1               5
```

PREPARATION METHOD OF HIGH-STABILITY SUPEROXIDE DISMUTASE WITH TRANSMEMBRANE CAPABILITY

CROSS REFERENCE TO RELATED APPLICATION

This patent application claims the benefit and priority of Chinese Patent Application No. 202110719256.8, filed on Jun. 28, 2021, the disclosure of which is incorporated by reference herein in its entirety as part of the present application.

INCORPORATION BY REFERENCE OF SEQUENCE LISTING

The Sequence Listing in an ASCII text file, named as 40384_Sequence_Listing.txt of 8 KB, created on Dec. 28, 2021, and submitted to the United States Patent and Trademark Office via EFS-Web, is incorporated herein by reference.

TECHNICAL FIELD

The present disclosure belongs to the technical field of genetic modification of an enzyme preparation and particularly relates to a preparation method of a high-stability superoxide dismutase with a transmembrane capability.

BACKGROUND ART

Superoxide free radicals are main reasons of human diseases and aging. Normally, the free radicals in body have a small generation amount and can be removed in time by an antioxidant system. However, when the body receives strong external stimulation, such as microorganism invasion, disease, stay up, environmental pollutant stimulation, ultraviolet irradiation, ionizing radiation, etc., the free radicals cannot be removed in time and the body can be attacked by the free radicals to generate oxidative damage.

Based on the above phenomena, it is necessary to reasonably utilize an exogenous superoxide dismutase (SOD) at a proper time to block the invasion of the free radicals to human body, which is very important for maintaining health. However, there are four major bottleneck problems in a use aspect of the superoxide dismutase at present: firstly, the superoxide dismutase does not have enough high activity and cannot be added as a terminal product; secondly, the superoxide dismutase does not have good stability and the activity of the superoxide dismutase is certain when just added into the terminal product, gradually reduced along with the time lapse of links such as storage, transportation and the like, and free of activity when reaching hands of consumers; thirdly, the superoxide dismutase cannot be supplied in a manner of liquid, all provided in a freeze-dried powder form at present on the market, and is extremely inconvenient for quantitative redissolution in a use process; and fourthly, the superoxide dismutase is a biological macromolecule, has subunits with molecular weight of 20,000 or more, does not have good cell permeability, and is not easily absorbed by cells and used for removing superoxide free radicals in the cells.

Therefore, there is a need to overcome the above disadvantages. The present disclosure discloses a high-stability superoxide dismutase with a transmembrane capability and truly enables the superoxide dismutase to be applied in terminal products (including antioxidant skin-care products, skin medicines, etc.).

SUMMARY

In order to overcome the above disadvantages, the present disclosure truly enables a superoxide dismutase to be applied in terminal products (including antioxidant skin-care products, skin medicines, etc.) aiming at the four bottleneck problems mentioned in the background art.

Firstly, the present disclosure realizes the high activity of the superoxide dismutase and can enable the activity of each milliliter of a superoxide dismutase solution to reach fifty thousand units.

In FIG. 16, according to a WST-8 activity measurement method, when the superoxide dismutase in an activity measurement system can inhibit an auto-oxidation rate of WST-8 by approximately 50%, the measured enzyme activity is the most accurate. As shown in the above figure, the superoxide dismutase has the enzyme activity of 50,000 U/mL or more.

Secondly, the present disclosure realizes the high stability of the superoxide whose half-life can reach one year or more at room temperature. Even in a high temperature environment of 50° C., the activity can still be maintained for 60 days or more as shown in FIG. 17.

Thirdly, the present disclosure realizes the liquid supply, liquid storage and liquid transportation of the superoxide dismutase.

Most importantly, the present disclosure realizes the transmembrane capability of the superoxide dismutase.

The present disclosure solves the technical problems by following technical schemes:

A preparation method of a high-stability superoxide dismutase with a transmembrane capability includes the following steps: extracting mRNA from *Geobacillus stearothermophilus*, synthesizing cDNA by a reverse transcription method, amplifying a large number of coding regions of the cDNA by designing a specific primer, ligating the coding regions to an *E. coli* expression vector, and transforming the coding regions into engineering bacteria BL21 (DE3).

The present disclosure explores an induction condition and expresses a protein with an enzymatic activity but not high enough stability. The present disclosure utilizes a point mutation technology to modify a sequence and discloses the sequence with a greatly improved thermal stability after exploring. The present disclosure modifies a transmembrane capability, utilizes a transmembrane peptide capable of crossing a cell membrane, explores a flexible linker ligating the transmembrane peptide and a superoxide dismutase, and discloses a highly active and highly stable superoxide dismutase with a transmembrane capability.

*Geobacillus stearothermophilus* is facultative anaerobic bacteria with a strong antioxidant capacity. The strain *Geobacillus stearothermophilus* deposited in China Center of Industrial Culture Collection (CICC) has No. CICC 10267 and is an American Type Culture Collection (ATCC) 7953 strain. The colony is cultured on a nutrient agar at 56° C. for 24 h and pale yellow and has a rough and moist surface and irregular edges.

Specifically, a preparation method of a high-stability superoxide dismutase with a transmembrane capability may include the following steps:

(1) designing a specific primer sequence
extracting a sequence encoding the superoxide dismutase from natural *Geobacillus stearothermophilus*;

(2) successfully ligating the sequence of the superoxide dismutase cloned in (1) to a prokaryotic expression vector and designing a primer for identifying a positive clone;

(3) obtaining an expression strain,
where the superoxide dismutase cloned from the *Geobacillus stearothermophilus* has an amino acid sequence as follows (SEQ ID NO: 1):

MPFELPALPYPYDALEPHIDKETMNIHHTKHHNTYVTNLNAALEGHPDL

QNKSLEELLSNLEALPESIRTAVRNNGGGHANHSLFWTILSPNGGGEPT

GELADAINKKFGSFTAFKDEFSKAAAGRFGSGWAWLVVNNGELEITSTP

NQDSPIMEGKTPILGLDVWEHAYYLKYQNRRPEYIAAFWNVVNWDEVAK

RYSEAKAK;
and the above sequence is the key protection content of the present disclosure;

(4) mutating aspartic acid at position 20 to glycine and mutating leucine at position 141 to asparagine by using a point mutation kit of NEB company; and (5) coupling a cell penetrating peptide (CPP) sequence YGRKKRRQRRR (SEQ ID NO: 10) with a transmembrane capability on an HIV-1 peptide segment with the superoxide dismutase for expression to enable the superoxide dismutase to have the transmembrane capability by using a flexible polypeptide linker GGGSGGGS (SEQ ID NO: 11).

After D20G and L141N are subjected to point mutations and the flexible polypeptide linker GGGSGGGS (SEQ ID NO: 11) may be used for a fusion expression of a YGRKKRRQRRR (SEQ ID NO: 10) sequence and the superoxide dismutase, the superoxide dismutase may have an amino acid sequence as follows (SEQ ID NO: 7):

```
MPFELPALPYPYDALEPHIGKETMNIHHTKHHNTYVTNLNAALEGHPDL

QNKSLEELLSNLEALPESIRTAVRNNGGGHANHSLFWTILSPNGGGEPT

GELADAINKKFGSFTAFKDEFSKAAAGRFGSGWAWLVVNNGENEITSTP

NQDSPIMEGKTPILGLDVWEHAYYLKYQNRRPEYIAAFWNVVNWDEVAK

RYSEAKAKGGGSGGGSYGRKKRRQRRR;
and
``` the above sequence is the key protection content of the present disclosure.

Preferably, in step (1) of designing the specific primer sequence, an RNA extraction kit may be used to extract the mRNA from the *Geobacillus stearothermophilus*, a reverse transcription kit may be used to synthesize the cDNA of the microorganism, a specific primer may be optimized according to restriction endonuclease sites, and the sequence encoding the superoxide dismutase may be captured and the optimized specific primer may have sequences as follows:

a captured upstream primer sequence for the superoxide dismutase:

```
                                      (SEQ ID NO: 2)
5'-CATATGCCCTTTGAACTACCAGCAT-3',
and
``` a captured downstream primer sequence for the superoxide dismutase:

```
                                      (SEQ ID NO: 3)
5'-AAGCTTCTTCGCTTTCGCCTCGCTG-3'.
```

The captured sequence may be the coding sequence of the superoxide dismutase to be expressed in the next step, which is the key point of the present disclosure (SEQ ID NO: 4):

```
ATGCCCTTTGAACTACCAGCATTACCCTATCCCTATGATGCTCTAGAAC

CGCACATTGACAAGGAGACCATGAACATCCACCACACCAAGCACCACAA

CACCTACGTGACCAACCTGAACGCGGCGCTGGAGGGTCACCCGGACCTG

CAGAACAAAAGCCTGGAGGAACTGCTGAGCAACCTGGAGGCGCTGCCGG

AAAGCATCCGTACCGCGGTTCGTAACAACGGTGGCGGTCACGCGAACCA

CAGCCTGTTTTGGACCATCCTGAGCCCGAACGGCGGTGGCGAGCCGACC

GGTGAACTGGCGGACGCGATTAACAAGAAATTCGGCAGCTTTACCGCGT

TCAAGGATGAGTTTAGCAAAGCGGCGGCGGGTCGTTTCGGTAGCGGTTG

GGCGTGGCTGGTTGTGAACAACGGCGAGCTGGAAATCACCAGCACCCCG

AACCAGGACAGCCCGATCATGGAGGGCAAGACCCCGATTCTGGGCCTGG

ATGTGTGGGAACACGCGTACTATCTGAAATACCAAAACCGTCGTCCGGA

ATATATTGCGGCGTTCTGGAATGTGGTGAACTGGGACGAGGTGGCGAAG

CGTTACAGCGAGGCGAAAGCGAAGTGAAAGCTT.
```

Preferably, in step (2), a pET30a vector may be selected as the expression vector, an amplified sequence and the vector may be digested with HindIII and NdeI, an obtained digested product may be recovered with a DNA gel recovery kit, the recovered digested product may be ligated with a DNA ligase at 16° C. for 12 h at a ratio of a DNA fragment and a plasmid of 2:1, a ligated linker may be transformed into competent the competent *E. coli* engineering bacteria BL21 (DE3) by heat shock at 42° C., the transformed engineering bacteria may be spread on an LB-resistant plate containing 50 μg/mL of kanamycin and incubated at 37° C. for 18-26 h to form a single clone and the clone may be verified; and a primer for colony PCR may have sequences as follows:

an upstream primer sequence for colony PCR: 5'-TTACCCTATCCCTATGATGCTC-3' (SEQ ID NO: 5), and a downstream primer sequence for colony PCR: 5'-CCCAACCGCTACCGAAAC-3' (SEQ ID NO: 6).

Preferably, in step (3) of obtaining the expression strain, a correctly verified single clone may be selected for an expression verification and specifically an expression condition may be as follows: 5 mL of a LB liquid medium may be inoculated with a monoclonal colony, the medium may contain 50 μg/mL of kanamycin, when an OD600 value reaches 0.7, IPTG may be added to a final concentration of 0.5 mM, induction may be conducted at different temperatures, bacterial cells may be collected after the induction, an ultrasonic lysis may be conducted and each component may be detected by an electrophoresis by a sodium dodecyl sulphate-polyacrylamide gel electrophoresis (SDS-PAGE) method.

Preferably, an ultrasonic lysis may be conducted at an ultrasonic volume of 1 mL and specifically, may be conducted for 2 s and stopped for 3 s with a total ultrasonic time of 10 min.

Preferably, in (5), a flexible polypeptide linker GGGSGGGS (SEQ ID NO: 11) or GGGGS (SEQ ID NO: 12) or GGSGGS (SEQ ID NO: 13) or GGGGG (SEQ ID NO: 14) may be used for an coupling expression of the superoxide dismutase;

In step (3), an activity of the superoxide dismutase in a lysed supernatant may be determined in the following steps: determining the activity by a WST-8 method, purifying by a glycerin-assisted heating method, a salting-out method, an organic solvent precipitation method and a dialysis method, concentrating and then detecting the activity by a WST-8 kit method; and in a thermal stability test, placing the purified superoxide dismutase in a water bath at 4° C., 75° C., 80° C., 85° C., 90° C. and 95° C. for 3 h respectively and detecting the enzyme activity.

The glycerin-assisted heating method may include the following steps: heating to 75° C. in 15% glycerol to inactivate impure proteins.

The result of the activity test shows that even if a soluble protein is obtained, it is not necessary to obtain a viable enzyme; and it is verified by the experiment of the present disclosure that the obtained enzyme by the method has better thermal stability, relatively high enzyme activity at 75° C., and still good stability with a gradually increased temperature.

The present disclosure has the following beneficial effects:
(1) mRNA is extracted from *Geobacillus stearothermophilus*, cDNA is synthesized by a reverse transcription manner, a specific primer designed to amplify a large number of coding regions of the cDNA, the coding regions are ligated to an *E. coli* expression vector, the coding regions are transformed into engineering bacteria BL21 (DE3), and after aspartic acid at position 20 is mutated to glycine and leucine at position 141 is mutated to asparagine, the thermal stability of the enzyme is maximized; and
(2) a CPP sequence YGRKKRRQRRR (SEQ ID NO: 10), that is a trans-activating transcriptional activator, with a transmembrane capability on an HIV-1 peptide segment is coupled with the superoxide dismutase for expression to enable the superoxide dismutase to have the transmembrane capability.

The final results show that the superoxide dismutase of the present disclosure has excellent thermal stability, a denaturant tolerance performance, an anti-enzymatic performance, and pH stability in a wide range; and in a mouse sunburn repair model, it is verified that the superoxide dismutase provided in the present disclosure has an excellent repair effect on the skin after sun exposure.

BRIEF DESCRIPTION OF THE DRAWINGS

FIG. 3 shows an expression of a target protein in a designed system by the present disclosure identified by using an SDS-PAGE method;
FIG. 4 shows determination of an activity of a superoxide dismutase by using a WST-8 method.

DETAILED DESCRIPTION OF THE EMBODIMENTS

To energy enable those skilled in the art to better understand the present disclosure, the present disclosure further stated in conjunction with specific embodiment.

The kits or raw materials used in the present disclosure have the following manufacturers or purchasing channels:
1. an RNA extraction kit, a reverse transcription kit and a DNA gel recovery kit: Tiangen Biotech;
2. a pET30a vector: Youbio;
3. a kit for determining activity by a WST-8 method: purchased from Beyotime;
4. HindIII and NdeI: purchased from Abclonal; and
5. a point mutation Q5 site-directed mutagenesis kit: purchased from NEB (New England BioLabs) company.

Example 1

A preparation method of a high-stability superoxide dismutase with a transmembrane capability included the following steps.
(1) an RNA extraction kit (purchased from Tiangen Biotech) was used to extract mRNA from *Geobacillus stearothermophilus*, a reverse transcription kit (purchased from Tiangen Biotech) was used to synthesize the cDNA of the microorganism, a specific primer (the primer sequence was as follows) was optimized according to restriction endonuclease sites, and the sequence encoding the superoxide dismutase was captured.

A captured upstream primer sequence for the superoxide dismutase was:

(SEQ ID NO: 2)
5'-CATATGCCCTTTGAACTACCAGCAT-3',
and a captured downstream primer sequence for the superoxide dismutase was:

(SEQ ID NO: 3)
5'-AAGCTTCTTCGCTTTCGCCTCGCTG-3'.

Figure 1:
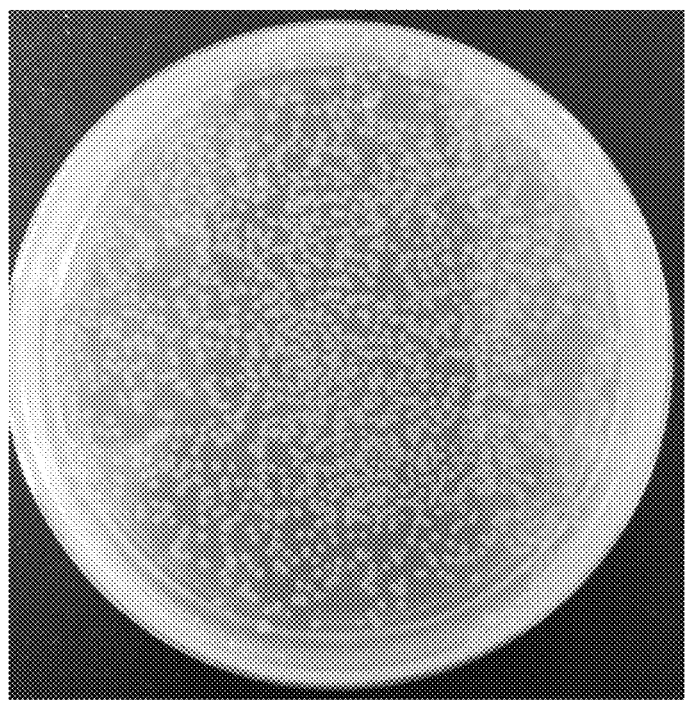
FIG. 1 is a photo of a monoclonal colony.
Figure 2:
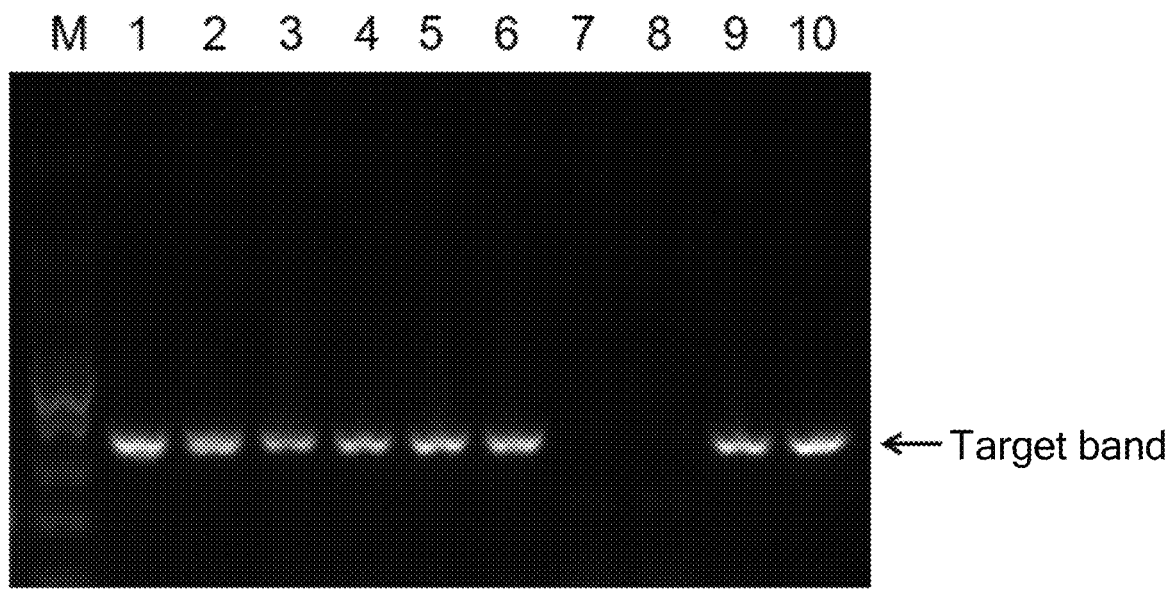
FIG. 2 shows identification of positive clones by colony PCR.

(2) A pET30a vector (purchased from Youbio) was selected as the expression vector, an amplified sequence and the vector were digested with HindIII and NdeI (purchased from Abclonal), an obtained digested product was recovered with a DNA gel recovery kit (purchased from Tiangen Biotech), the recovered digested product was ligated with a DNA ligase at 16° C. for 12 h at a molar ratio of a DNA fragment and a plasmid of 2:1, a ligated linker was transformed into the competent E. coli engineering bacteria BL21 (DE3) by heat shock at 42° C., and the transformed engineering bacteria were spread on an LB-resistant plate containing 50 μg/mL of kanamycin and incubated at 37° C. for 18-26 h to form a single clone; after the single clone was formed (FIG. 1), a colony PCR method was used (sequences of colony PCR primers as follows) to verify the clone (FIG. 2).

FIG. 1 is a diagram of ligation of an amplified superoxide dismutase fragment and the expression vector. A ligated linker was transformed into competent E. coli engineering bacteria BL21 (ED3), and the transformed engineering strain was spread on an LB-resistant plate containing 50 μg/mL of kanamycin and incubated at 37° C. for 24 h to form a single-clone colony;

FIG. 2 shows identification of positive clones by a colony PCR method, where 1, 2, 3, 4, 5, 6, 9 and 10 are positive clones.

An upstream primer sequence for colony PCR was: 5'-TTACCCTATCCCTATGATGCTC-3' (SEQ ID NO: 5); and a downstream primer sequence for colony PCR was: 5'-CCCAACCGCTACCGAAAC-3' (SEQ ID NO: 6).

(3) A correctly verified single clone was selected for an expression verification and specifically an expression condition was as follows: 5 mL of a LB liquid medium (the medium contains 50 μg/mL of kanamycin) was inoculated with a monoclonal colony, when an OD600 value reached 0.7, IPTG was added to a final concentration of 0.5 mM (a preferred concentration), and induction was conducted at different temperatures (preferably, 16° C. and 37° C.); bacterial cells were collected after the induction and an ultrasonic lysis was conducted at an ultrasonic volume of 1 mL and specifically, was conducted for 2 s and stopped for 3 s with a total ultrasonic time of 10 min.

After the experiment, each component was detected by an electrophoresis by using an SDS-PAGE method (FIG. 3).

FIG. 3 shows an expression of a target protein in a designed system by the present disclosure identified by using the SDS-PAGE method; Lane 1 and Lane 2 in FIG. 3 were the 5th component (BSA-V) spotted with different amounts of bovine serum albumin (BSA) and technical internal references, indicating that the SDS-PAGE was in good working; from Lane 3 to Lane 5 in the figure, the system expressed the target protein well; from Lane 6 to Lane 8 in the figure, the target protein expressed by the system had fair solubility; from Lane 9 to Lane 11 in the figure, the target protein expressed by the system had certain inclusion bodies; comparing Lane 8 and Lane 11, the protein expressed by the system was soluble proteins, which enabled the protein to have an anti-oxidation ability;

FIG. 3 proves that the protein obtained by the present disclosure is solublely expressed, which is a key step for the success of the present disclosure; if the solublely expressed protein cannot be obtained or the obtained protein was insoluble, it proves that the method has no practical use significance.

An activity of the superoxide dismutase in an obtained lysate supernatant was determined by using a WST-8 method (a kit was purchased from Beyotime). After the activity was determined, a purification method was explored. A glycerin-assisted heating method (heating to 75° C. in 15% glycerol to inactivate impure proteins), a salting-out method, an organic solvent precipitation method and a dialysis method were used for purification, and a WST-8 kit method was used to detect the activity and the activity was 24,747 U/mL (See FIG. 4).

FIG. 4 uses the WST-8 method to determine the activity of the superoxide dismutase. According to the kit instructions, when an absorbance value of a sample tube to be tested reaches ½ of a positive oxidation tube, the measured data is the most accurate. As shown in the figure, a first hole represents a "negative oxidation tube control" not containing an oxidation starter; a second hole represents the positive oxidation tube (oxygen free radicals could catalyze a substrate to produce yellow products and darker yellow color meant more severe oxidation); third to sixth holes almost has no color, indicating that the enzyme activity is too high to be accurately estimated; in a seventh hole and an eighth hole, the measured value is close to ½ of the positive oxidation tube; and after calculation, the activity is 24,747-28,055 U/mL.

Figure 5:
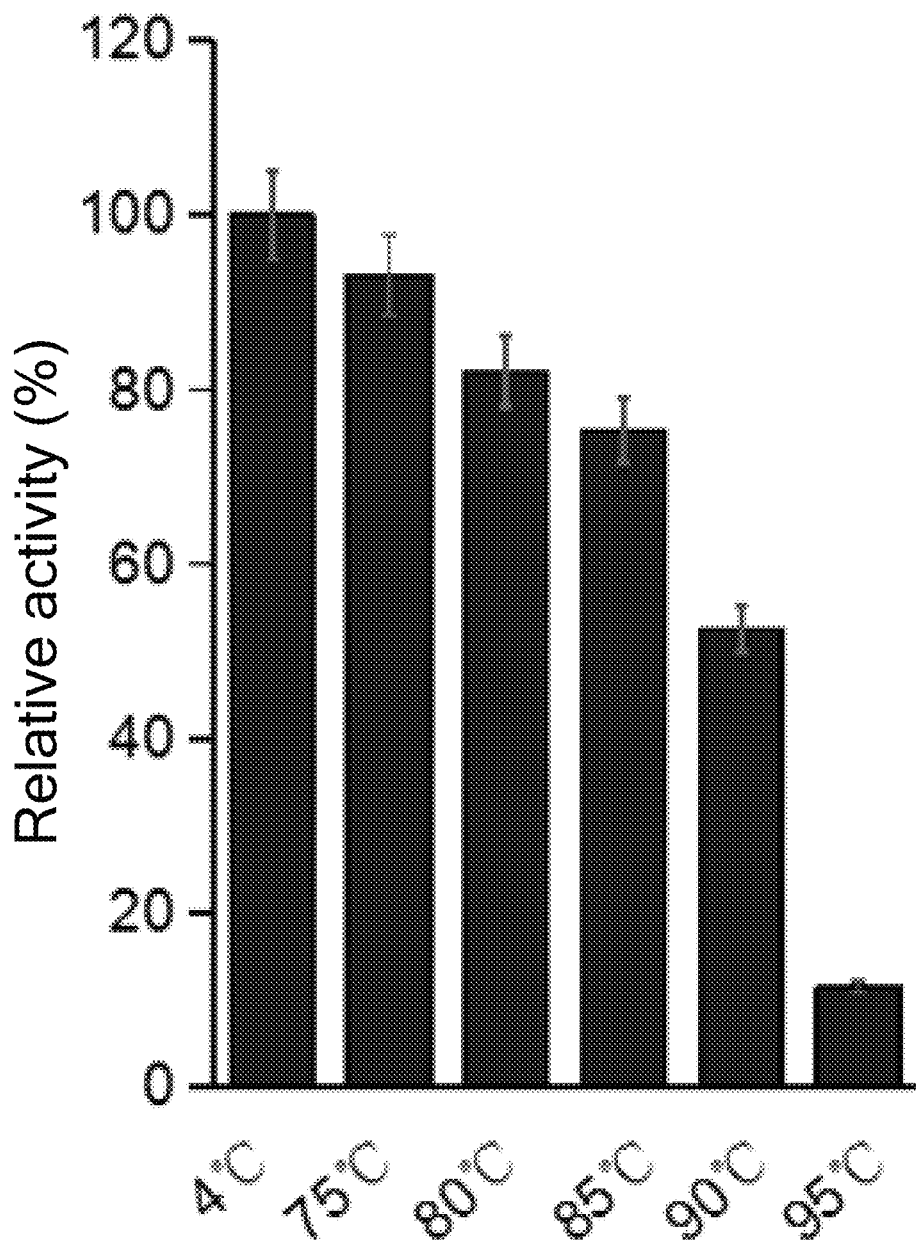
FIG. 5 shows the activity the superoxide dismutase measured after the superoxide dismutase obtained in the present disclosure is incubated at different temperatures.

In a thermal stability test, the purified superoxide dismutase was placed in a water bath 4° C., 75° C., 80° C., 85° C., 90° C. and 95° C. for 3 h respectively and the enzyme activity was detected (See FIG. 5). FIG. 5 shows the superoxide dismutase obtained in the present disclosure, and the activity of the superoxide dismutase was measured by using the WST-8 method after the superoxide dismutase was incubated in water bath at different temperatures for 3 h respectively. It was concluded from FIG. 5 that the enzyme obtained by the present disclosure had relatively good thermal stability but lost the activity significantly when the temperature exceeded 80° C.;

(4) Stability of the superoxide dismutase is improved.

Figure 6:
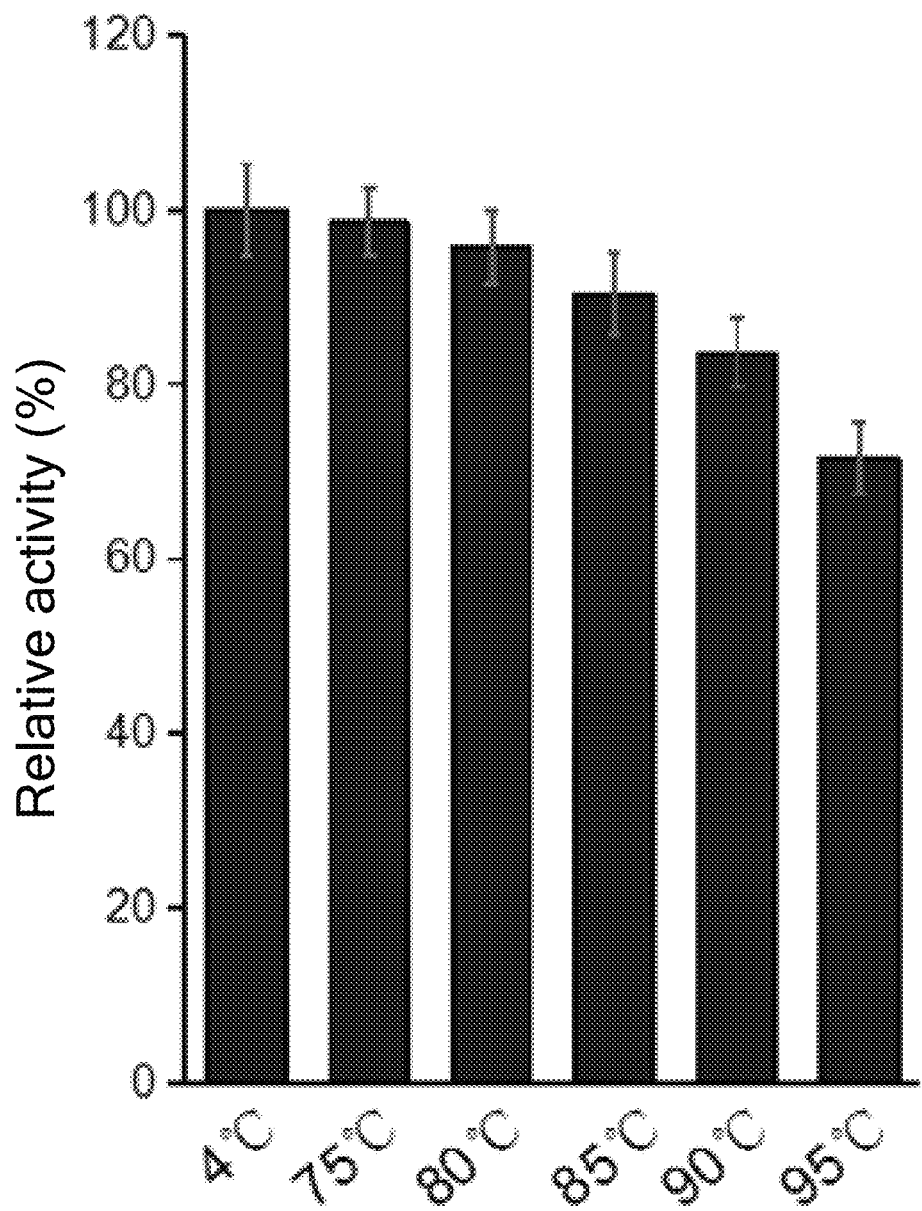
FIG. 6 shows the activity the superoxide dismutase measured after the superoxide dismutase obtained by using a point mutation modification is incubated at different temperatures.
Figure 7:
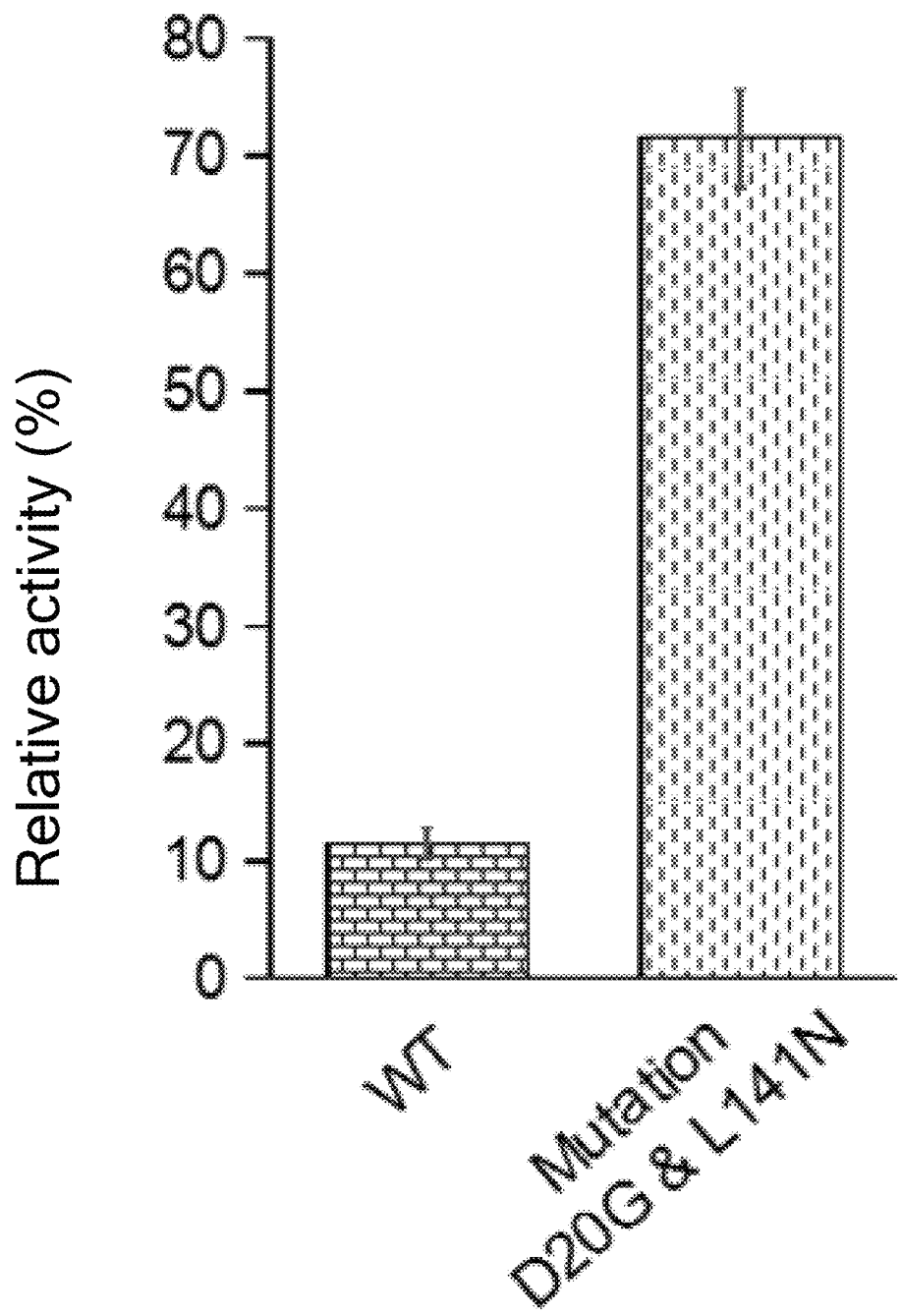
FIG. 7 shows comparison of thermal stability before and after mutation of D20G&L141N.

In order to improve the thermal stability of the superoxide dismutase, characteristics of an amino acid sequence were analyzed, key amino acid sites having an impact on the thermal stability were screened out, and the superoxide dismutase was mutated to improve the thermal stability; after a pre-test experiment and study, it was finally found that after aspartic acid at position 20 was mutated to glycine and leucine at position 141 was mutated to asparagine, the thermal stability of the enzyme could be maximized (FIG. 6 and FIG. 7).

FIG. 6 shows the superoxide dismutase obtained after the modification by the point mutation, and the activity of the superoxide dismutase was measured by using the WST-8 method after the superoxide dismutase was incubated in water bath at different temperatures for 3 h respectively. It could be seen from the result histogram that the enzyme of the present disclosure had an excellent thermal stability and had the activity not decreased by more than 20% even if heated in an environment of 90° C. for 3 h; and FIG. 7 compares the thermal stability before and after the mutation of D20G&L141N. From the result histogram, it could be seen that after the sequence was mutated the thermal stability was greatly enhanced.

(5) The transmembrane capability of the superoxide dismutase is improved.

The cell membrane has a natural barrier function, and specifically can maintain a relatively stable intracellular environment and regulate and select substances entering and leaving the cell. The cell membrane is composed of a bilayer of phospholipids, such that non-fat-soluble substances, polypeptides and protein biological macromolecules cannot enter the cell freely. Due to the barrier function of the cell membrane, many medicinal biologically active macromolecules in vitro cannot enter the cell. It was analyzed that the superoxide dismutase did not have a transmembrane signal region and thus had extremely low transmembrane capability; the present disclosure needed to develop a superoxide dismutase with a transmembrane capability.

Recently, it is found that a class of short peptides, namely CPPs, are capable of spontaneously crossing the cell membranes and carrying biological macromolecules into cells, and have a relatively strong transmembrane capability; the CPPs are a class of short peptides composed of tens of amino acids, can deliver biologically active substances into cells to exert biological activity and produce therapeutic effects, do not cause permanent damage to cell membranes, and are non-irritating, such that the CPPs are used as a highly favored new drug delivery vehicle. A CPP sequence YGRKKRRQRRR (SEQ ID NO: 10), that was a trans-activating transcriptional activator, with a transmembrane capability on an HIV-1 peptide segment was coupled with the superoxide dismutase for expression to enable the superoxide dismutase to have the transmembrane capability. However, a problem of protein expression spatial conformation should be considered when a coupling expression was conducted. In order to prevent the CPP sequence from affecting the correct spatial conformation of the superoxide dismutase, a flexible polypeptide linker-GGGSGGGS (SEQ ID NO: 11) (other optional flexible polypeptide linkers GGGGS (SEQ ID NO: 12), GGSGGS (SEQ ID NO: 13) and GGGGG (SEQ ID NO: 14)) was introduced in the present disclosure to maximize a soluble expression and a transmembrane secretion expression of the coupled superoxide dismutase (FIG. 8).

Figure 8:
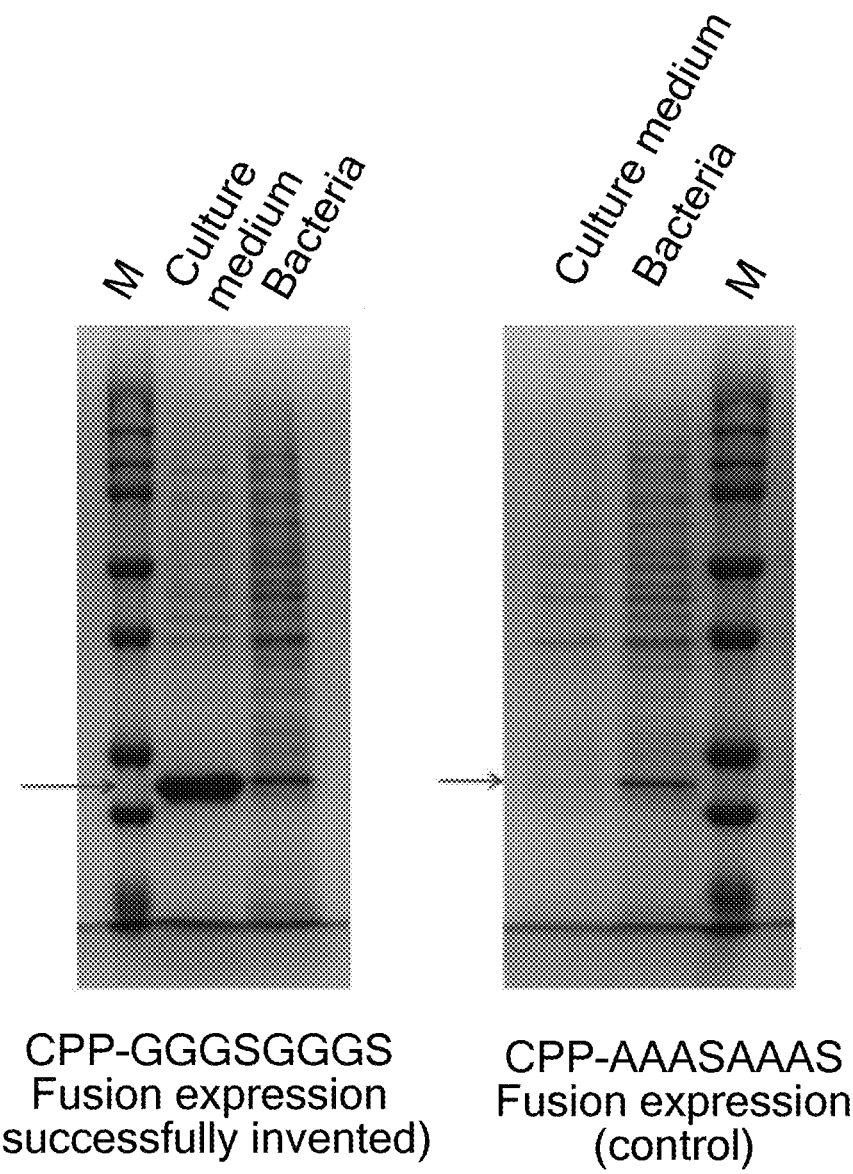
FIG. 8 shows a soluble expression and a transmembrane secretion expression of the coupled superoxide dismutase after introducing "a transmembrane peptide and a flexible polypeptide linker GGGSGGGS (SEQ ID NO: 11)"

FIG. 8 shows the maximized soluble expression and the transmembrane secretion expression of the coupled superoxide dismutase after introducing "a transmembrane peptide and a flexible polypeptide linker GGGSGGGS (SEQ ID NO: 11)".

It could be seen from FIG. 8 that the left picture shows that the transmembrane peptide and flexible polypeptide linker GGGSGGGS (SEQ ID NO: 11) was added, and a target protein was concentrated in the culture medium instead of mainly in the bacteria. As a control, the transmembrane peptide and an AAASAAAS (SEQ ID NO: 15) sequence were added in the right picture, however a desired effect cannot be achieved. A red arrow marked location of the target protein.

A method for introducing the flexible peptide linker and the CPP sequence was as follows: the Q5 Site-directed mutagenesis kit was purchased from the NEB company, primers were designed as follows, the ability of a high-fidelity ultra-length DNA polymerase Q5 was used to amplify a plasmid in a reverse manner, and KLD brought by the kit connected the newly amplified plasmid into a circle.

Primer 1 was as follows:

(SEQ ID NO: 8)
5'-CCATAACTTCCTCCTCCACTTCCTCCTCCAAGCTTTCACTTCGCTT
TCG-3';

Primer 2 was as follows:

(SEQ ID NO: 9)
5'-TCGTAAGAAGCGCCGTCAACGTCGCCGTATTCGCCGGCCTGAGCT
C-3'.

The flexible peptide linker and the CPP sequence were used for the coupled expression with the superoxide dismutase to achieve the soluble expression and the transmembrane secretion expression, and then the thermal stability (FIG. 9), the pH stability (FIG. 10), the denaturant tolerance (FIG. 11), the resistance to enzymatic hydrolysis (FIG. 12) and the compatibility with potassium sorbate (FIG. 13) of the obtained product was continuously verified. The results showed that the superoxide dismutase had good thermal stability and could maintain more than 80% of the activity even if heated at a high temperature of 90° C. for 3 h.

Figure 9:
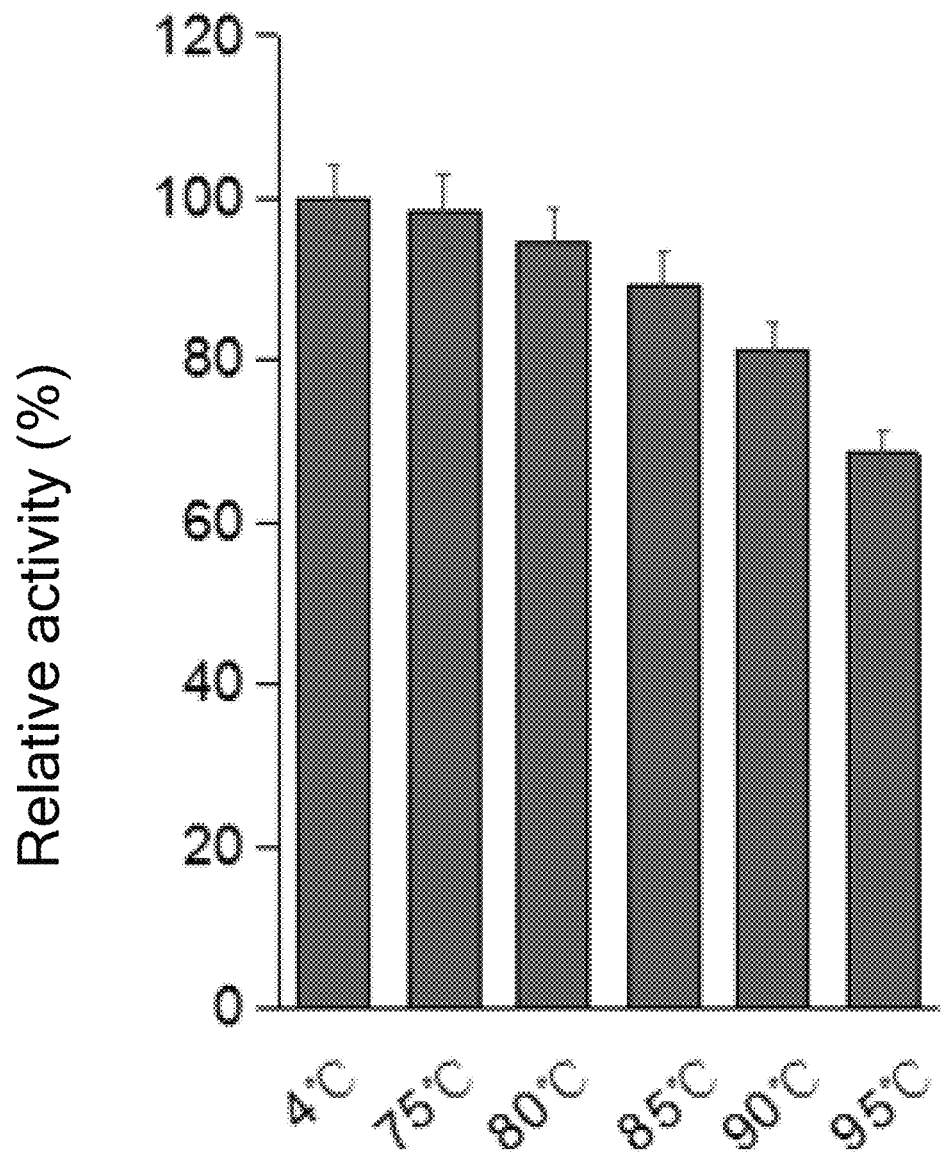
FIG. 9 shows a verification of a thermal stability effect after introducing "a transmembrane peptide and the flexible polypeptide-GGGSGGGS (SEQ ID NO: 11)"

FIG. 9 shows the verification of the thermal stability after introducing "the transmembrane peptide and the flexible polypeptide GGGSGGGS". As shown in the figure, the superoxide dismutase had excellent thermal stability.

Figure 10:
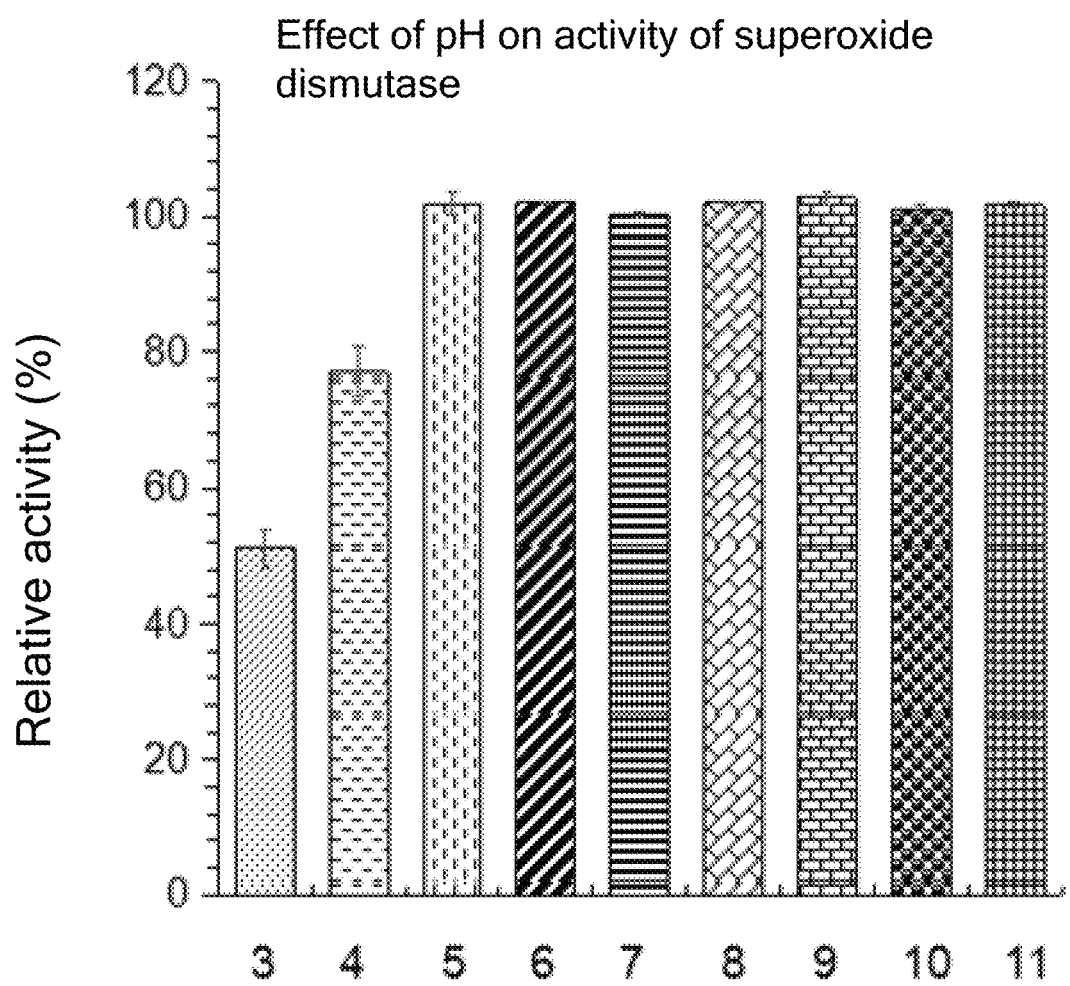
FIG. 10 shows the tolerance of the superoxide dismutase of the present disclosure to different pH environments.

FIG. 10 shows the tolerance of the superoxide dismutase of the present disclosure to different pH environments. It could be seen from the result histogram that the superoxide dismutase could tolerate a wide range of pH, especially had strong tolerance to alkaline environments, was relatively weak tolerance to acidic environments, and could maintain vitality only in weakly acidic environments.

Figure 11:
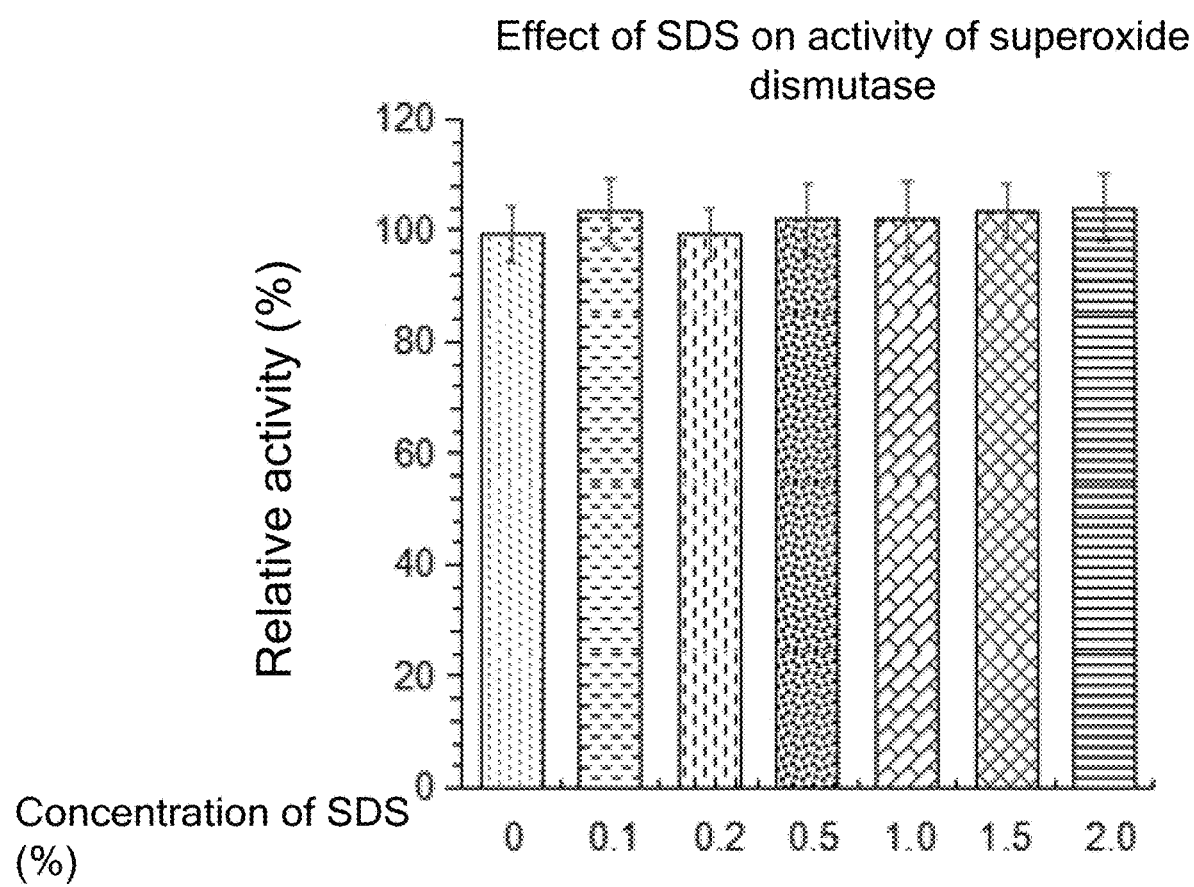
FIG. 11 shows the tolerance of the superoxide dismutase of the present disclosure to a denaturant SDS.

FIG. 11 shows the tolerance of the superoxide dismutase of the present disclosure to a denaturant SDS. It could be seen from the result histogram that the superoxide dismutase had very strong tolerance to the ionic surfactant SDS and could be applied in products such as daily chemical products.

Figure 12:
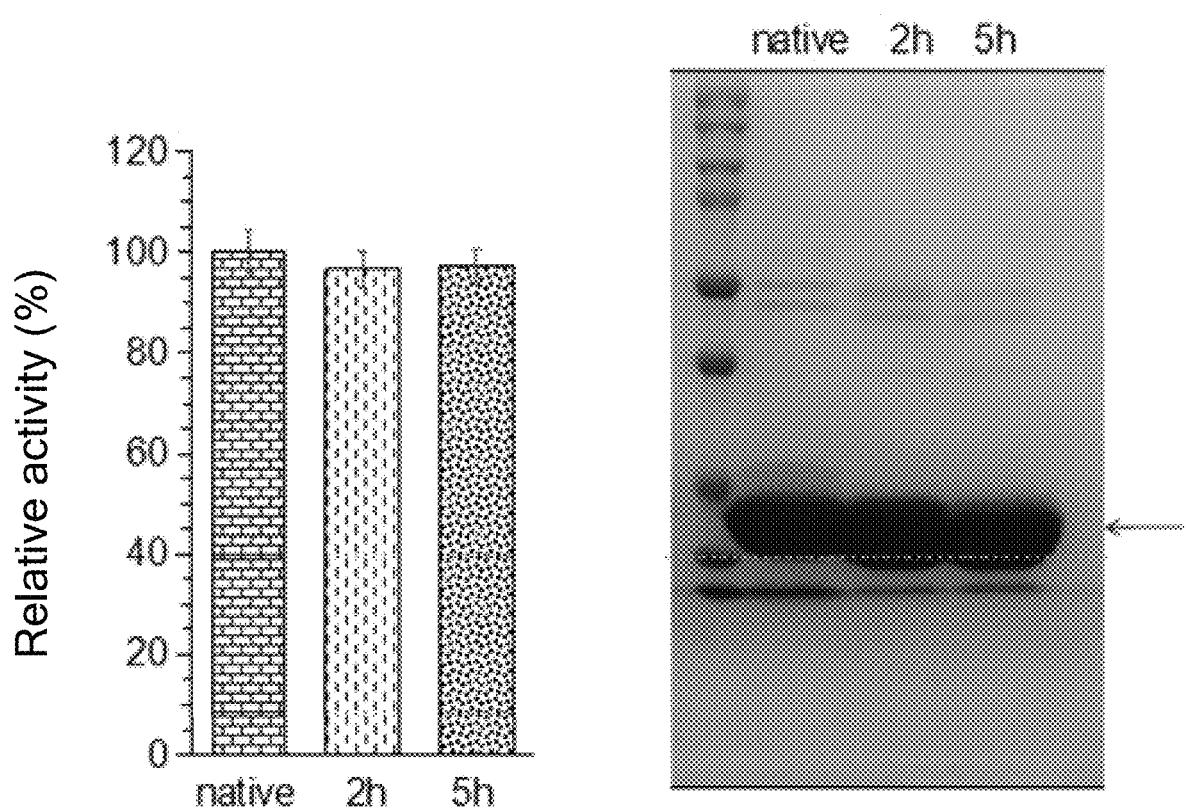
FIG. 12 shows the tolerance of the superoxide dismutase of the present disclosure to a digestive enzyme.

FIG. 12 shows the tolerance of the superoxide dismutase of the present disclosure to a digestive enzyme. 2 h and 5 h respectively represented digestion by a trypsin (purchased from Gibco) for 2 h and for 5 h. It could be seen from the result histogram that the superoxide dismutase had strong tolerance to the trypsin and the vitality of the superoxide dismutase was not weakened even in a high concentration of the trypsin for digestion for 5 h (left picture). The molecular weight of the superoxide dismutase would decrease slightly with the extension of trypsin digestion time, but the vitality remained unchanged, which indicated that the trypsin could only degrade a part of side chains of the superoxide dismutase, but did not affect an active center.

Figure 13:
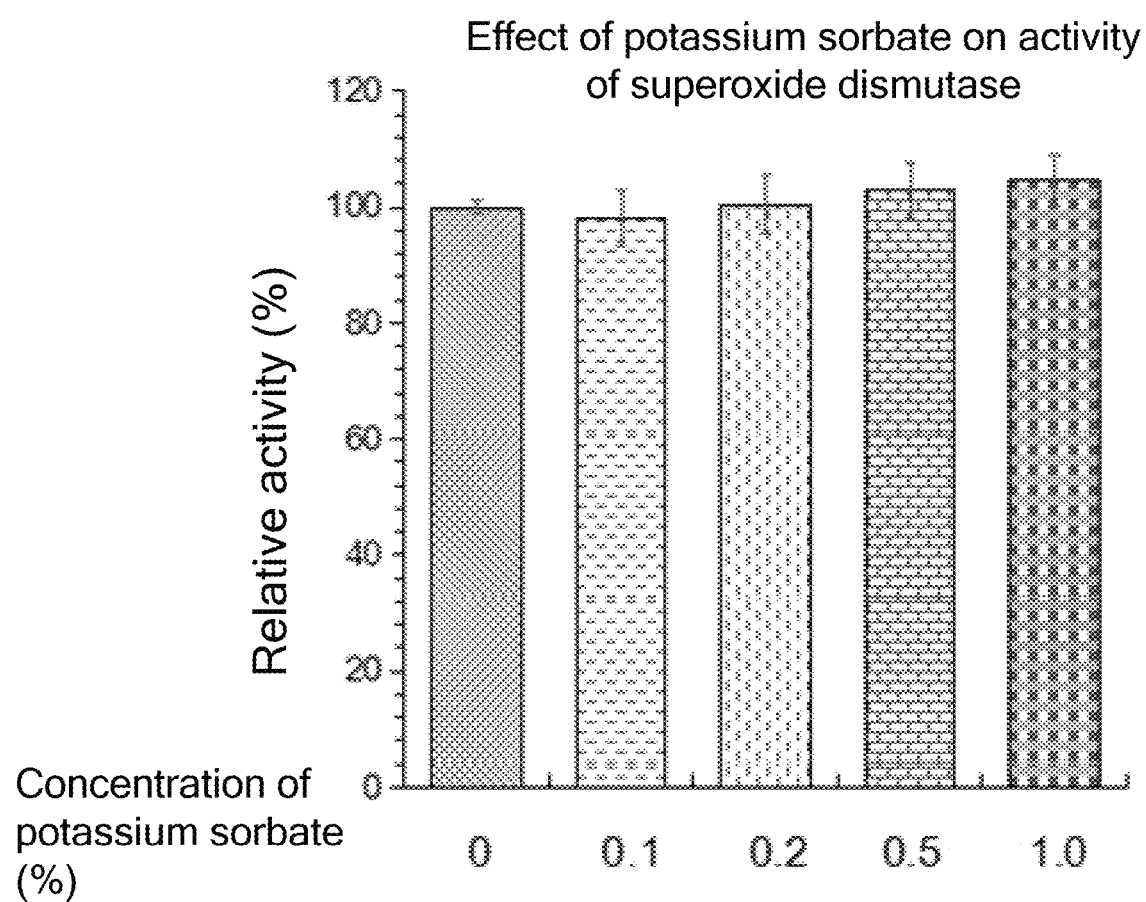
FIG. 13 shows the tolerance of the superoxide dismutase of the present disclosure to a preservative potassium sorbate.

FIG. 13 shows the tolerance of the superoxide dismutase of the present disclosure to a preservative potassium sorbate. The potassium sorbate was a commonly used preservative in food and cosmetics, and had a common final use concentration of 0.05%-0.2%. After the superoxide dismutase was incubated with different concentrations of the potassium sorbate for 24 h, the enzyme activity was detected. It could be seen from the result histogram that the superoxide dismutase had a good compatibility with the potassium sorbate and the activity of the superoxide dismutase was not weakened even incubated in a high concentration of the potassium sorbate for 24 h, which indicated that in the terminal product containing the superoxide dismutase, the potassium sorbate could be used as a preservative.

Figure 14:
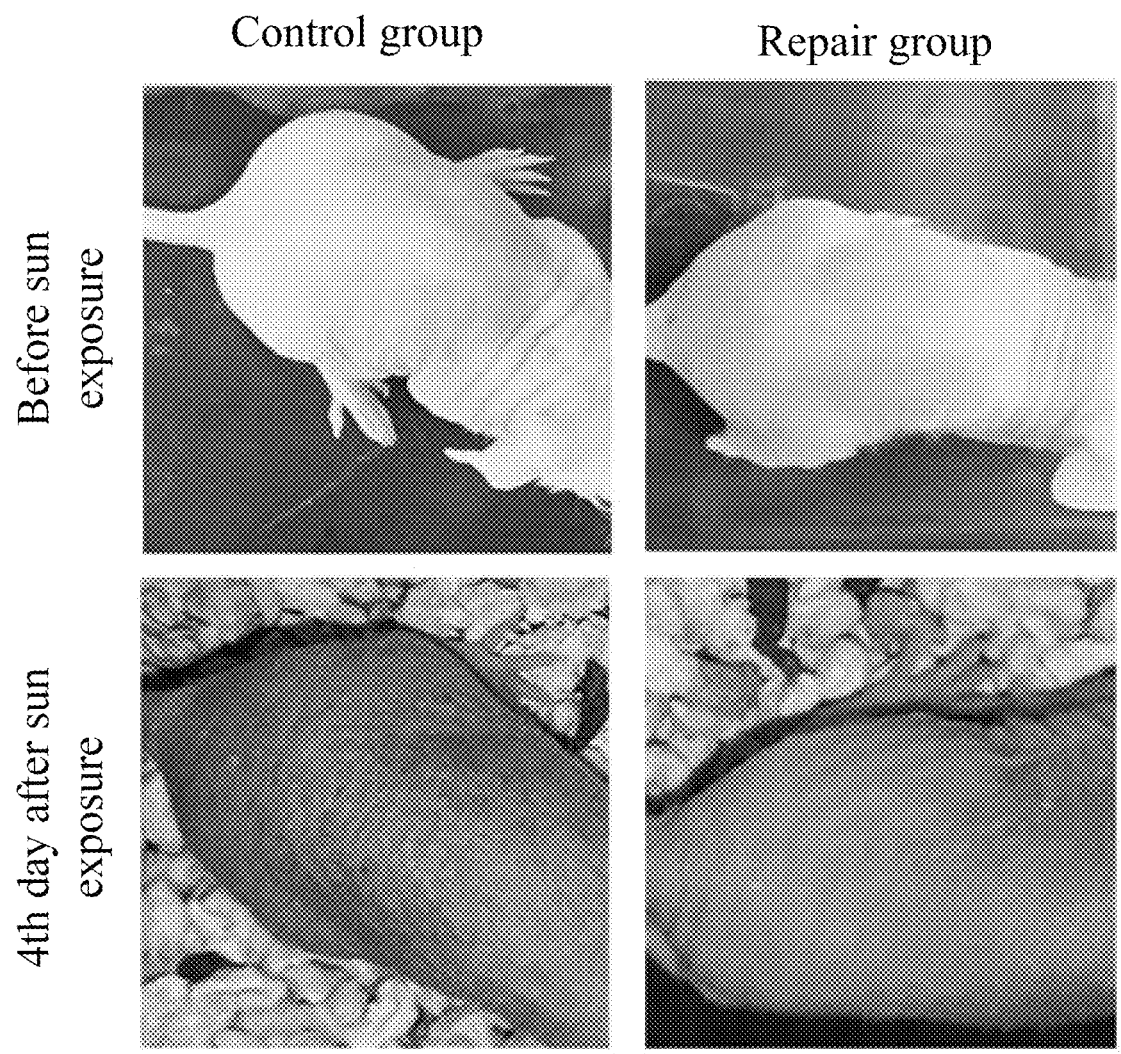
FIG. 14 shows the verification of the function of the superoxide dismutase of the present disclosure on skin repair after sun exposure.
Figure 15:
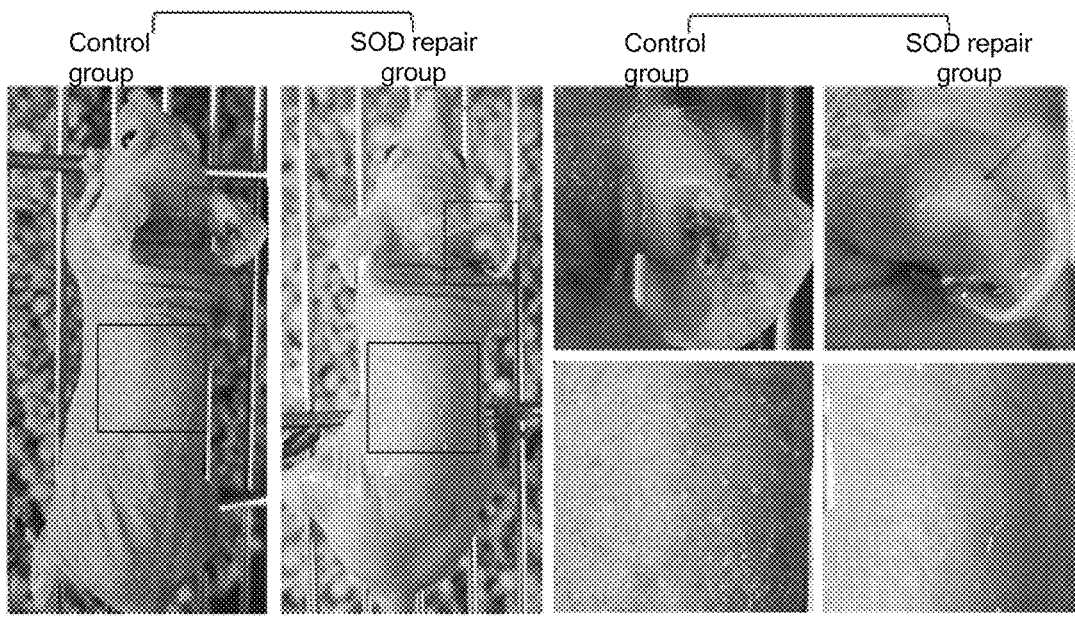
FIG. 15 shows the verification of the effect of the superoxide dismutase of the present disclosure on repairing and preventing solar dermatitis.
Figure 16:
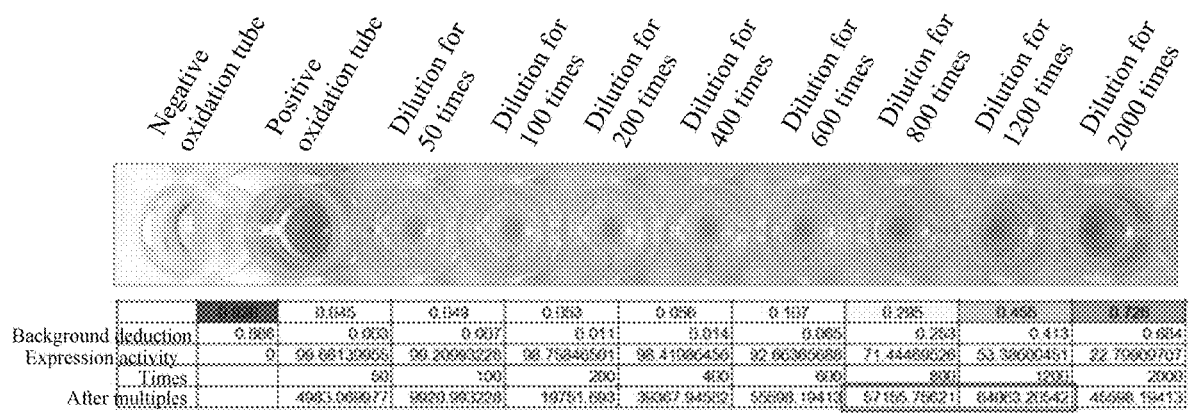
FIG. 16 shows the superoxide dismutase of the present disclosure having the enzyme activity of 50,000 U/mL or more.
Figure 17:
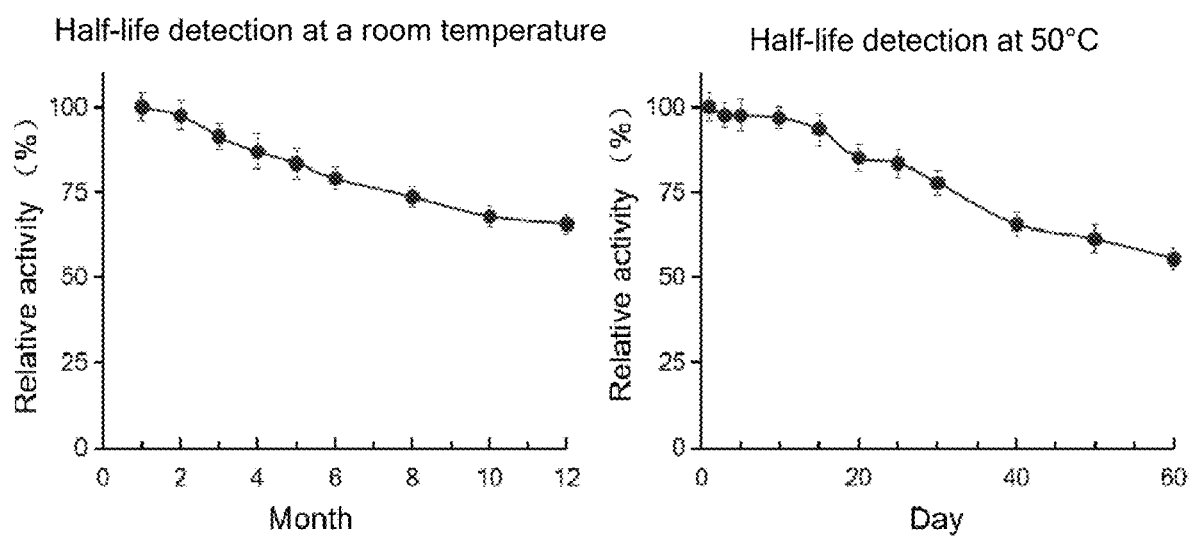
FIG. 17 shows half-life test results at room temperature and 50° C.

After an excellent enzymatic performance of the superoxide dismutase was verified, in a mouse sunburn repair model, the repair effect of the superoxide dismutase after sun exposure was verified (FIG. 14 and FIG. 15). The superoxide dismutase could scavenge oxygen free radicals. Since ultraviolet radiation would enable the skin to produce a large number of free radicals, after nude mice were subjected to ultraviolet radiation, a repair experiment was used to verify after transdermal absorption and antioxidant properties of the superoxide dismutase;

FIG. 14 shows the verification of the function of the superoxide dismutase of the present disclosure on skin repair after sun exposure. Two groups of the nude mice (BalB/C nude) were irradiated with ultraviolet rays for 45 min, respectively. After the sun exposure, the mice in a repair group were quickly applied with 200 μl of the superoxide dismutase with the activity of 300 U/mL, while the mice in a control group were not applied with the product. After 4 days, there were obvious differences in the skin of the nude mice: the skin of the nude mice in the control group had obvious browning, wrinkling, hardening, etc., while the skin of the nude mice in the repair group remained healthy. It could be seen that the product could effectively repair skin problems caused by the ultraviolet radiation.

FIG. 15 shows the functions of the superoxide dismutase of the present disclosure on repairing and preventing solar dermatitis. Two groups of the nude mice were irradiated with ultraviolet rays for 40 min each day. After the sun exposure, the mice in the repair group were quickly applied with 200 μl of the superoxide dismutase with the activity of 300 U/mL, while the mice in the control group were not applied with the product. After the operation was repeated for 3 days, the solar dermatitis occurred in the control group, while the skin of the mice in the repair group had no abnormalities. It could be seen that the product could effectively repair the solar dermatitis caused by the ultraviolet radiation.

What is claimed is:

1. A method of preparing a superoxide dismutase with a transmembrane capability, comprising the following steps:
  (1) extracting mRNA from *Geobacillus stearothermophilus*, synthesizing cDNA by a reverse transcription method, designing a specific primer sequence, amplifying a large number of coding regions of the cDNA with the specific primer sequence to obtain a sequence encoding the superoxide dismutase from natural *Geobacillus stearothermophilus*, ligating the coding regions to an *E. coli* expression vector, and transforming the *E. coli* expression vector into engineering bacteria BL21 (DE3) to clone a sequence of the superoxide dismutase;
  (2) ligating the sequence of the superoxide dismutase cloned in (1) to a prokaryotic expression vector and designing a primer for identifying a positive clone;
  (3) obtaining an expression strain, wherein the superoxide dismutase cloned from the *Geobacillus stearothermophilus* has the amino acid sequence as follows (SEQ ID NO: 1):

```
MPFELPALPYPYDALEPHIDKETMNIHHTKHHNTYVTNLNAALEGHPDL

QNKSLEELLSNLEALPESIRTAVRNNGGGHANHSLFWTILSPNGGGEPT

GELADAINKKFGSFTAFKDEFSKAAAGRFGSGWAWLVVNNGELEITSTP

NQDSPIMEGKTPILGLDVWEHAYYLKYQNRRPEYIAAFWNVVNWDEVAK

RYSEAKAK;
```

(4) mutating aspartic acid at position 20 to glycine and mutating leucine at position 141 to asparagine; and
  (5) coupling a cell penetrating peptide (CPP) sequence YGRKKRRQRRR (SEQ ID NO: 10) with a transmembrane capability on an HIV-1 peptide segment with the superoxide dismutase for expression to enable the superoxide dismutase to have the transmembrane capability, wherein the CPP sequence is a trans-activating transcriptional activator sequence.

* * * * *